United States Patent
Smith

(12) 
(10) Patent No.: US 6,184,209 B1
(45) Date of Patent: Feb. 6, 2001

(54) DIABETES TREATMENT

(75) Inventor: Margaret Elizabeth Smith, Birmingham (GB)

(73) Assignee: Alizyme Therapeutics Limited, Cambridge (GB)

( * ) Notice: Under 35 U.S.C. 154(b), the term of this patent shall be extended for 0 days.

(21) Appl. No.: 09/142,699

(22) PCT Filed: Mar. 21, 1997

(86) PCT No.: PCT/GB97/00795

§ 371 Date: Feb. 4, 1999

§ 102(e) Date: Feb. 4, 1999

(87) PCT Pub. No.: WO97/35608

PCT Pub. Date: Oct. 2, 1997

(30) Foreign Application Priority Data

Mar. 22, 1996 (GB) .................................. 9606076

(51) Int. Cl.$^7$ ............................ A61K 38/05; A61K 38/07
(52) U.S. Cl. ................................. 514/19; 514/15; 514/16; 514/17; 514/18; 514/866
(58) Field of Search ................... 514/2, 18, 19, 514/15, 16, 17, 866

(56) References Cited

U.S. PATENT DOCUMENTS 5,561,110 * 10/1996 Michaelis et al. ...................... 514/3

FOREIGN PATENT DOCUMENTS 4244639  7/1994 (DE) .
4312913  10/1994 (DE) .

OTHER PUBLICATIONS

Richter et al., Endocrin, vol. 120, No. 4, pp. 1472–1476, 1987.*

R. L. Reid et al., "B–Endorphin Stimulates the Secretion of Insulin and Glucagon in Diabetes Mellitus", *Metabolism,* vol. 33, No. 3, Mar. 1984; pp. 197–199.

Samantha Jeal et al., "Effect of B–endorphin on glucose uptake in vitro in insulin–resistant muscles of obese–diabetic (ob/ob) mice", *The Journal of Physiology,* vol. 491P, 1996, 3 pages.

R. J. Carter et al., "Melanotropin potentiating factor is the C–terminal tetrapeptide of human B–lipotropin", *Nature,* vol. 279, No. 5708, May 3, 1979, pp. 74–75.

J. S. Morley et al., "MPF Analogue With High Stability to Proteolysis", *Neuropeptides* vol. 2, 1981, pp. 109–114.

J.S. Morley et al., "Structural Specificity of Beta–Endorphin C–Terminal Tetrapeptide (MPF) in Promoting Urodele Limb Regeneration", *Life Sciences,* vol. 45, Aug. 2, 1989, pp. 1341–1347.

* cited by examiner

Primary Examiner—Bennett Celsa
(74) Attorney, Agent, or Firm—Wells, St. John, Roberts, Gregory & Matkin, P.S.

(57) ABSTRACT

Diabetes Mellitus type I or II is treated by use of a peptide including an amino acid sequence comprising part of a 10 amino acid C-terminal fragment of β-endorphin.

19 Claims, No Drawings

SEQUENCE LISTING

<160> NUMBER OF SEQ ID NOS: 2

<210> SEQ ID NO 1
<211> LENGTH: 4
<212> TYPE: PRT
<213> ORGANISM: mammalian

<400> SEQUENCE: 1

Lys Lys Gly Gln
 1

<210> SEQ ID NO 2
<211> LENGTH: 4
<212> TYPE: PRT
<213> ORGANISM: mammalian

<400> SEQUENCE: 2

Lys Lys Gly Glu

DIABETES TREATMENT

CROSS-REFERENCES TO RELATED APPLICATIONS

This patent claims priority to International Application Number is PCT/GN97/00795, filed Mar. 21, 1997; which claims priority to GB Patent Application Serial No. 9606076.9, filed Mar. 22, 1996.

BACKGROUND OF THE INVENTION a. Field of the Invention

This invention relates to diabetes treatment and is more particularly concerned with diabetes mellitus. The present invention is considered to be suitable for the treatment of either type I (insulin-dependent) or type II (non-insulin-dependent) diabetes mellitus.

b. Description of the Related Art

It has been observed by R. L. Reid et al ("β-endorphin stimulates the secretion of Insulin and Glucagon in Diabetes Mellitus", Metabolism, Vol 33, No 3 (March), 1984, pages 197–199) that administration of human β-endorphin (2.5 mg by intravenous bolus injection) to three subjects with non-insulin dependent diabetes mellitus (type II) induced prompt and simultaneous increments in the plasma concentrations of insulin and glucagon lasting up to 90 minutes and that, in contrast to the hyperglycemic response previously observed in normal subjects following administration of β-endorphin, these diabetics showed a progressive decline in plasma glucose throughout a three hour study period. However, this progressive decline in plasma glucose was substantially unaffected by the administration of β-endorphin which took place one hour after the start of the study period.

It has been observed by the inventor that, in normal mice, there are only a small number of β-endorphin receptors on the muscle fibres, whereas in obese (ob/ob) diabetic mice, there is a dramatically higher density of β-endorphin receptors on the muscles. The obese (ob/ob) mice inherit diabetes mellitus which resembles type II (non-insulin-dependent) diabetes mellitus seen in humans. In both the human and the mouse with this condition, the muscles are insulin-resistant. The present invention is based on the surprising discovery that blood glucose levels can be reduced by administration of β-endorphin fragments which do not include the opioid (N-terminal) region of β-endorphin, and that such fragments act by enhancing the uptake of glucose into the muscle by a non-insulin dependent route.

BRIEF SUMMARY OF THE INVENTION

The invention encompasses a method of treating a patient with diabetes mellitus. The patient is administered an effective amount of a an amino acid sequence having one or more amino acid residues in common with a ten amino acid C-terminal fragment of β-endorphin, and having one or more amino acid residues different than the C-terminal fragment of β-endorphin. The peptide comprises no more than 10 amino acid residues, and the fragment has X-Y as the final two amino acid residues at the C-terminal end. The X of X-Y is Gly, Sar, AzGly, Ala, D-Ala, D-Ser or Pro; and the Y is Glu or Gin.

DETAILED DESCRIPTION OF THE INVENTION

The present invention resides in the use of a peptide including an amino acid sequence corresponding to that of an active C-terminal fragment of β-endorphin or an active analogue of a C-terminal fragment of β-endorphin, in the manufacture of a medicament for the treatment of diabetes mellitus (type I or II).

The present invention also resides in the use of a peptide including an amino acid sequence corresponding to that of an active C-terminal fragment of β-endorphin or an active analogue of a C-terminal fragment of β-endorphin, in the manufacture of a medicament for increasing uptake of blood glucose into muscle.

The term "active" refers to the activity for the uses intended in the present invention.

The peptide preferably has β-endorphin 31 (Glu or Gin) as the C-terminal amino acid residue. More preferably, the peptide includes or consists of at least β-endorphin 30–31 (Gly-Glu or Gly-Gln), even more preferably β-endorphin 29–31 (Lys-Gly-Glu or Lys-Gly-Gln), and most preferably β-endorphin 28–31 (Lys-Lys-Gly-Glu (SEQ ID NO:2) or Lys-Lys-Gly-Gln (SEQ ID NO:1)). However, it is within the scope of the present invention for the peptide to include further amino acid residues in its N-terminal region. For example, the peptide may be β-endorphin 22–31, 23–31, 24–31, 25–31, 26–31 or 27–31.

The peptide preferably has no more than 10 amino acid residues, but more preferably has less, eg up to nine, eight, seven, six or five amino acid residues; or even more preferably, less than six amino acid residues, Thus, most preferably, the peptide is a di-, tri-, tetra- or penta-peptide.

The use of active analogues of the above-mentioned peptides is also within the scope of the present invention. In particular, stabilised analogues thereof are preferred wherein one or more of the following substitutions may be made:

| Amino Acid | Substituting moiety |
| --- | --- |
| 28 (Lys) | Orn, MeLys, des-NH$_2$, Nle or D-Lys |
| 29 (Lys) | Orn, D-Lys, MeLys or Nle |
| 30 (Gly) | Sar, AzGly, Ala, D-Ala, D-Ser or Pro |
| 31 (Glu) | Gln |

(wherein 28 to 31 relate to the numbering for the corresponding amino acids in the β-endorphin amino acid sequence).

One of hydrogen atoms at the N-terminal end of the peptide (preferably the 28-N-terminal end of β-endorphin 28–31) may be substituted by P-Ala, HOOC(CH$_2$)$_2$CO—, Tyr, benzylcarbonyl, maionyl, acetyl, fatty acid acyl or other acyl group. Hereinafter, these acyl groups will be referred to as Ac.

Of such analogues, those where amino acid 30 (Gly) is replaced by Sar, those where amino acid 29 (Lys) is replaced by D-Lys, and those where the N-terminal (28) end of the fragment is Ac-Lys, are preferred. Particularly preferred is the stabilised analogue in which all three substitutions have been made, i.e. Ac-Lys-D-Lys-Sar-Glu, most preferably CH$_3$CO-Lys-D-Lys-Sar-Glu or CH$_3$CO-Lys-D-Lys-Sar-Gln.

Furthermore, the above peptides are small molecules compared to insulin (or β-endorphin). The stabilised analogues include those which are stable to proteolytic digestion and therefore have a relatively long half-life in the blood enabling their actions to be long lasting. Their resistance to proteolytic digestion may also make them effective via oral administration. In addition, the peptides usable in the present invention do not contain the opioid amino acid sequence and therefore are not likely to have those side effects of β-endorphin which are due to its opioid actions.

β-endorphin 28–31 is a per se known compound and is sometimes referred to as melanotrophin-potentiating factor (MPF). It is a putative neurotrophic agent. Stabilised analogues of MPF, such as Ac-Lys-D-Lys-SarGlu, are also known, see for example J. S. Morley et al in "MPF analogue with high stability to proteolysis", Neuropeptides 2:109–114, 1981 and D. M. Ensor et al, Brain Research, 610 (1993), pages 166–168. The latter report MPF and Ac-Lys-D-Lys-Sar-Glu as causing significant reductions on the turning response of dopamine-depleted rats to D-amphetamine. MPF and certain analogues thereof are also reported as promoting urodele limb regeneration (see J. S. Morley et al, Life Sciences, Vol. 45, pages 1341–1347).

The peptides used in the present invention can be administered intravenously, subcutaneously or intramuscularly, although stabilised analogues, such as Ac-Lys-D-Lys-Sar-Glu, may possibly be administered orally.

The peptides used in the present invention can be synthesised in a per se known manner, for example by use of the solid-phase method of R. Bruce Merrifield where amino acids are added stepwise to a growing peptide chain linked to an insoluble resin matrix, using (i) dicyclohexylcarbodi-imide to activate the carboxyl groups to be subjected to peptidisation at the appropriate stages, and (ii) a t-butyloxycarbonyl group and trifluoroacetic acid respectively to block and deblock the amino groups to be protected at the appropriate stages during synthesis.

In the case of the N-substituted peptides noted above, N-substitution may also be effected in a manner known per se by a simple peptidisation reaction with appropriate blocking, if necessary, depending upon the nature of the substituent group.

The invention further resides in a method of treating a patient with diabetes, comprising the step of administering to such patient an effective amount of a peptide as defined above.

The invention also resides in a method of increasing uptake of blood glucose into muscle in a patient, comprising the step of administering to such patient an effective amount of a peptide as defined above.

The peptides may be administered in amounts in the range of 0.1 to 100 nmoles of peptide per kg body weight, more preferably 1 to 10 nmoles/kg body weight.

The present invention is based on sets of experiments whose results are reported in the following Examples.

EXAMPLE 1

Isolated soleus, EDL (extensor digitorum longus) or diaphragm muscles of normal male and female mice were incubated for 30 min at 37° C. in oxygenated Krebs buffer containing 2-deoxy-D-[1-$^3$H]glucose. 2-Deoxy-D-glucose is a derivative of D-glucose which is taken up into muscle by carrier-mediated transport and which accumulates in muscle as 2-deoxy-D-glucose-6-phosphate without further metabolism. The tritiated derivative can therefore be used to determine the uptake into muscle of D-glucose (which itself is metabolised). A COOH-terminal (C-terminal) fragment of β-endorphin and an analogue of a β-endorphin fragment were added to the Krebs buffer. These were the C-terminal dipeptide (glycyl-L-glutamine or glycyl-L-glutamic acid) and $CH_3CO$-Lys-D-Lys-Sar-Glu, a stable analogue of the C-terminal tetrapeptide of β-endorphin. Pyruvate (2 mM) and 2% bovine serum albumen were also present in the bathing medium surrounding the muscles. The extracellular space in the muscles was determined by including L-[1-$^{14}$C] glucose, which is not transported into muscle via the D-glucose membrane carrier.

At the end of the incubation period, the tissue samples were digested in 1 M NaOH at 90° C. and the radioactivity counted by liquid scintillation counting.

There was an increase in the uptake of 2-deoxy-D-glucose into the muscles in the presence of either of these peptides.

a) Isolated soleus muscles—male mice $CH_3CO$-Lys-D-Lys-Sar-Glu was effective at concentrations of $10^{-11}$ M, $10^{-10}$ M and $10^{-9}$ M. At $10^{-9}$ M, $CH_3CO$-Lys-D-Lys-Sar-Glu produced a 9-fold (800%) increase in the uptake of 2-deoxy-D-glucose into the muscles. In comparison, insulin at $10^{-9}$ M gave only a 6-fold (500%) increase.

b) Isolated soleus muscles—female mice $CH_3CO$-Lys-D-Lys-Sar-Glu was effective at concentrations of $10^{-8}$ M and $10^{-7}$ M. At $10^{-8}$ M, $CH_3CO$-Lys-D-Lys-Sar-Glu produced an approximately 2-fold (100%) increase in the uptake of 2-deoxy-D-glucose into the muscles. Insulin at $10^{-8}$ M (optimum concentration) gave a similar approximately 2-fold (100%) increase.

c) EDL muscles—male mice $CH_3CO$-Lys-D-Lys-Sar-Glu at a concentrations of $10^{-9}$ M produced a 7-fold (600%) increase in the uptake of 2-deoxy-D-glucose into the muscles. In comparison, insulin at $10^{-9}$ M gave only a 2.5-fold (150%) increase.

d) EDL muscles—female mice $CH_3CO$-Lys-D-Lys-Sar-Glu was effective at concentrations of $10^{-6}$ M, $10^{-7}$ M and $10^{-8}$ M. At $10^{-7}$ M, $CH_3CO$-Lys-D-Lys-Sar-Glu produced a 7-fold (600%) increase in the uptake of 2-deoxy-D-glucose into the muscles. In comparison, insulin at $10^{-7}$ M gave only a 3.5-fold (250%) increase.

e) Diaphragm muscles—female mice $CH_3CO$-Lys-D-Lys-Sar-Glu was effective at concentrations of $10^{-7}$ M, $10^{-8}$ M and $10^{-9}$ M. At $10^{-8}$ M, $CH_3CO$-Lys-D-Lys-Sar-Glu produced a 4-fold (300%) increase in the uptake of 2-deoxy-D-glucose into the muscles, which is similar to that produced by insulin at the same concentration.

EXAMPLE 2

Following the procedure outlined in Example 1, it was shown that Gly-Gln in a concentration of $10^{-7}$ M caused a 180% increase in 2-deoxy-D-glucose uptake in EDL muscles of normal female mice, whilst with Gly-Glu there was an 80% increase.

EXAMPLE 3

Following the procedure outlined in Example 1, it was shown that $CH_3CO$-Lys-D-Lys-Sar-Glu in a concentration of $10^{-7}$ M caused an approximately 2-fold increase in 2deoxy-D-glucose uptake in soleus muscles of obese-diabetic (ob/ob) mice.

EXAMPLE 4

Following the procedure outlined in Example 1 using neonatal normal mouse abdominal muscle strips, it was shown that $CH_3CO$-Lys-D-Lys-Sar-Glu caused increases in the uptake of 2-deoxy-D-glucose into the muscle strips at concentrations of $10^{-8}$ M, $10^{-9}$ M and $10^{-10}$ M, the increase being 40% at $10^{-10}$ M.

EXAMPLE 5

In another experiment on the muscles of obese-diabetic mice, following the procedure outlined in Example 1, it was shown that $CH_3CO$-Lys-D-Lys-Sar-Glu in a concentration of $10^{-7}$ M caused a 70% increase in 2-deoxy-D-glucose uptake in the EDL muscles of these obese-diabetic mice.

EXAMPLE 6

Following the procedure outlined in Example 1 using rat L6 cells (a commercially available cell line derived from rat muscle), it was shown that $CH_3CO$-Lys-D-Lys-Sar-Glu was effective at concentrations of $10^{-12}$ M to $10^{-8}$ M. At $10^{-9}$ M, $CH_3CO$-Lys-D-Lys-Sar-Glu produced an approximately 40% increase in the uptake of 2-deoxy-D-glucose into the muscles.

In the presence of $10^{-8}$ M insulin, $CH_3CO$-Lys-D-Lys-Sar-Glu at a concentration of $10^{-9}$ M caused a 30% increase in glucose uptake over that produced by the insulin alone.

From the above, it will be understood that the peptide acts to increase the uptake of blood glucose into muscle independently of insulin. Thus, it is considered that the present invention is also suitable as an alternative to insulin administration for the treatment of type I diabetes mellitus.

Key

Tyr=L-tyrosine; Lys=L-lysine; D-Lys=D-lysine; Ac=acyl, preferably acetyl; Orn=Lornithine; MeLys=N-α-methyl-lysine; des-$NH_2$=desamino-lysine; Nle=ε-amino group of lysine replaced by Me; AzGly=α-azaglycine; D-Ser=D-serine; Ala=L-alanine; D-Ala=D-alanine; Pro=proline; Sar=sarcosine, otherwise known as N-methyl-glycine (N-MeGly).

| Amino Acid | Substituting moiety |
|---|---|
| 28 (Lys) | Orn, MeLys, des-$NH_2$, Nle or D-Lys |
| 29 (Lys) | Orn, D-Lys, MeLys or Nle |
| 30 (Gly) | Sar, AzGly, Ala, D-Ala, D-Ser or Pro |
| 31 (Glu) | Gln | and wherein 28 to 31 are the numbering for amino acids in the β-endorphin amino acid sequence.

5. The method as claimed in claim 1, wherein a hydrogen at the N-terminal end of the peptide is substituted by a group selected from β-Ala, $HOOC(CH_2)_2CO$—, Tyr, benzylcarbonyl, malonyl, acetyl, fatty acid acyl and other acyl groups.

6. The method as claimed in claim 4, wherein the peptide includes Ac-Lys-D-Lys-Sar-Glu, where Ac is an acyl group.

7. The method as claimed in claim 4, wherein the peptide is $CH_3CO$-Lys-D-Lys-Sar-Glu.

8. The method as claimed in claim 1, wherein the peptide has no more than five amino acid residues.

9. A method of increasing uptake of blood glucose into muscle in a patient, comprising the step of administering to such patient an effective amount of a 2–10 amino acid

---

---

What is claimed is:

1. A method of treating a patient with diabetes mellitus, comprising the step of administering to such patient an effective amount of a peptide containing a 2–10 amino acid peptide analogue of β-endorphin 22–31 which comprises a dipeptide X-Y representing amino acids 30–31 of β-endorphin as its C-terminus and one or more N-terminal amino acids which are the same or different from amino acids 22–29 of β-endorphin; wherein X is Gly, Sar, AzGly, Ala, D-Ala, D-Ser or Pro; and wherein Y is Glu or Gln.

2. The method as claimed in claim 1, for the treatment of type II diabetes mellitus.

3. The method as claimed in claim 1, for the treatment of type I diabetes mellitus.

4. The method in claim 1, wherein the 2–10 amino acid peptide analogue of β-endorphin 22–31 comprises one or more of the following substitutions relative to β-endorphin:

peptide analogue of β-endorphin 22–31 which comprises a dipeptide X-Y representing amino acids 30–31 of β-endorphin as its C-terminus and one or more N-terminal amino acids which are the same or different from amino acids 22–29 of β-endorphin; wherein X is Gly, Sar, AzGly, Ala, D-Ala, D-Ser or Pro; and wherein Y is Glu or Gln.

10. A method of treating a patient with diabetes mellitus, comprising the step of administering to such patient an effective amount of a 2–10 amino acid peptide analogue of β-endorphin 22–31 which comprises a dipeptide X-Glu representing amino acids 30–31 of β-endorphin as its C-terminus; wherein X is an amino acid residue selected from the group consisting of Gly, Sar, AzGly, Ala, D-Ala, D-Ser and Pro.

11. The method of claim 10 wherein X is Gly.
12. The method of claim 10 wherein X is Sar.
13. The method of claim 10 wherein X is AzGly.
14. The method of claim 10 wherein X is Ala.

15. The method of claim 10 wherein X is D-Ala.
16. The method of claim 10 wherein X is D-Ser.
17. The method of claim 10 wherein X is Pro.
18. A method of treating a patient with diabetes mellitus, comprising the step of administering to such patient an effective amount of a 2–10 amino acid peptide analogue of β-endorphin 22–31 which comprises a tetra-peptide Ac-Lys-D-Lys-Sar-Glu representing amino acids 28–31 of β-endorphin as its C-terminus.

19. The method of claim 18 wherein the tetra-peptide is $CH_3CO$-Lys-D-Lys-Sar-Glu.

* * * * *